(12) United States Patent
Xu

(10) Patent No.: US 9,527,923 B2
(45) Date of Patent: Dec. 27, 2016

(54) METHODS OF INHIBITING PLATELET AGGREGATION AND PREVENTING THROMBOSIS USING ANTIBODIES THAT BIND (NA$^+$+K$^+$)-ATPASE β SUBUNIT

(71) Applicant: Kai Yuan Xu, Cockeysville, MD (US)

(72) Inventor: Kai Yuan Xu, Cockeysville, MD (US)

( * ) Notice: Subject to any disclaimer, the term of this patent is extended or adjusted under 35 U.S.C. 154(b) by 0 days.

(21) Appl. No.: 14/713,032

(22) Filed: May 15, 2015

(65) Prior Publication Data

US 2015/0259438 A1  Sep. 17, 2015

Related U.S. Application Data

(63) Continuation-in-part of application No. 13/359,723, filed on Jan. 27, 2012, now Pat. No. 9,040,046.

(60) Provisional application No. 61/437,719, filed on Jan. 31, 2011, provisional application No. 61/994,355, filed on May 16, 2014.

(51) Int. Cl.
*C07K 16/40* (2006.01)
*A61K 39/00* (2006.01)

(52) U.S. Cl.
CPC ......... *C07K 16/40* (2013.01); *A61K 2039/505* (2013.01); *C07K 2317/34* (2013.01); *C07K 2317/75* (2013.01); *C07K 2317/76* (2013.01)

(58) Field of Classification Search
CPC . C07K 16/40; C07K 2317/34; C07K 2317/75; C07K 2317/76; A61K 2039/505
See application file for complete search history.

(56) References Cited

U.S. PATENT DOCUMENTS

| 7,754,210 | B2 | 7/2010 | Xu | |
| 8,435,519 | B2 * | 5/2013 | Xu | A61K 39/0005 424/130.1 |
| 9,040,046 | B2 * | 5/2015 | Xu | C07K 16/40 424/133.1 |
| 9,238,695 | B2 * | 1/2016 | Xu | C07K 16/40 |

OTHER PUBLICATIONS

Moon et al., The inhibitory effect of plasma fibronectin on collagen-induced platelet aggregation.Blood 67(2):450-457, 1986.*
Golino et al.,Endothelium-derived relaxing factor modulates platelet aggregation in an in vivo model of recurrent platelet activation. Circ Res. 71(6):1447-1456, 1992.*
Young et al., Multiple mRNAs from rat kidney and brain encode a signle Na+, K+-ATPase beta subunit protein. J. Biol. Chem. 262:4905-4910, 1987.
Xu, Activation of (Na+ + K+)-ATPase. Biochem. Biophys. Res. Commun. 338:1669-1677, 2005.
Xu, Biochem. Allosteric property of the (Na+ + K+)-ATPase B1-subunit. Biophys. Res. Commun. 415:479-484, 2011.
Fambrough et al., Analysis of subunit assembly of the Na—K-ATPase. Am. J. Physiol. 266(3 Pt. 1):C579-589, 1994.
Schneider et al., Involvement of the M7/M8 extracellular loop of the sodium pump a subunit in ion transport. J. Biol. Chem. 272(26):16158-16165, 1997.
Wang et al., Valine 904, tyrosine 898, and cysteine 908 in Na,K-ATPase alpha subunits are important for assembly with beta subunits. J. Biol. Chem. 273(45):29400-29405, 1998.

* cited by examiner

*Primary Examiner* — Ruixang Li

(57) ABSTRACT

Methods of inhibiting platelet aggregation using antibodies having binding specificity for the β subunit of the (Na$^+$+K$^+$)-ATPase are provided, along with methods for inhibiting or preventing thrombosis in a subject using such antibodies.

3 Claims, 7 Drawing Sheets

METHODS OF INHIBITING PLATELET AGGREGATION AND PREVENTING THROMBOSIS USING ANTIBODIES THAT BIND (NA$^+$+K$^+$)-ATPASE β SUBUNIT

TECHNICAL FIELD

The invention relates to methods for inhibiting platelet aggregation and to methods for inhibiting and/or preventing thrombosis using antibodies that bind the β subunit of (Na$^+$+K$^+$)-ATPase (NKA).

BACKGROUND OF INVENTION

Thrombosis is the formation of a blood clot (thrombus) which comprises aggregated platelets and a mesh of cross-linked fibrin protein within a blood vessel. A thrombus can restrict blood flow to downstream tissues supplied by the blocked blood vessel. Thrombosis thus deprives the downstream tissue of oxygen and nutrients, and can cause infarction and tissue death. Thrombosis can cause myocardial infarction in the heart when the thrombosis involves a coronary artery supplying the heart, and can cause a stroke when the thrombosis involves a blood vessel in the brain. Depending upon the location of a blot clot within the circulatory system, thrombosis can also cause disease in the kidney, liver, extremities, and other bodily locations.

Antiplatelet medications are most effective at preventing arterial blood clots which are composed largely of platelets. Antiplatelet medications are administered to patients who have coronary artery disease, angina, heart failure, heart valve disease, or at risk for coronary artery disease or stroke, to help prevent a heart attack or stroke.

Thrombosis remains the world's largest single cause of mortality, despite the fact that medication has been available for over 50 years to treat and prevent the condition. Clearly, new treatments for thrombosis are needed.

BRIEF SUMMARY OF INVENTION (Na$^+$+K$^+$)-ATPase (NKA; the sodium pump) is a transmembrane enzyme responsible for the active reciprocal transport of Na$^+$ and K$^+$ ions across the plasma membrane of all animal cells. NKA comprises two basic subunits: the α subunit and the β subunit. The larger α subunit catalyzes the hydrolysis of ATP for active transport of Na$^+$ and K$^+$ ions across the plasma membrane; the smaller β subunit does not participate in the catalytic process of the enzyme, but instead acts as a specific chaperone that assists the biogenesis and correct membrane insertion of newly synthesized NKA.

The present invention is based on the surprising discovery that platelet aggregation can be inhibited using antibodies that bind the β subunit of NKA of platelets. Antibodies with β subunit binding specificity can be used to inhibit platelet aggregation, and inhibit or prevent thrombosis in a subject. Such antibodies thus form the basis of methods of treating or preventing blood clots associated with diseases such as stroke, myocardial infarction, deep vein thrombosis, and generally any venous or arterial thrombosis resulting from platelet aggregation and resulting in patient morbidity or mortality.

Examples of antibodies having β subunit binding specificity that can be used in the methods of the present invention include, but are not limited to, JY2948 and JY421228, humanized versions thereof, and fragments thereof. These antibodies are described in U.S. Patent Publication No. US 2012/0195886 (U.S. Pat. No. 9,040,046), which is herein incorporated by reference in its entirety for all purposes.

In a first aspect, the invention thus provides methods for inhibiting platelet activation comprising contacting platelets with an antibody having binding specificity for the β subunit of NKA. Exemplary antibodies that may be used in these methods include, but are not limited to, (i) antibodies having binding specificity for the β$_1$ subunit of NKA, (ii) antibodies having binding specificity for one or more of the peptides represented by SEQ ID NOs:1-4, (iii) antibody JY421228 or a humanized version thereof, or a fragment or derivative thereof, and (iv) antibody JY2948 or a humanized version thereof, or a fragment or derivative thereof. The method may be conducted in vitro or in vivo. The method may also be conducted in blood ex vivo.

In a second aspect, the invention provides methods for inhibiting platelet aggregation comprising contacting platelets with an antibody having binding specificity for the β subunit of NKA. Exemplary antibodies that may be used in these methods include, but are not limited to, (i) antibodies having binding specificity for the β$_1$ subunit of NKA, (ii) antibodies having binding specificity for one or more of the peptides represented by SEQ ID NOs:1-4, (iii) antibody JY421228 or a humanized version thereof, or a fragment or derivative thereof, and (iv) antibody JY2948 or a humanized version thereof, or a fragment or derivative thereof. The method may be conducted in vitro or in vivo. The method may also be conducted in blood ex vivo.

In a third aspect, the invention provides methods for inhibiting platelet aggregation in a subject comprising administering an effective amount of an antibody having binding specificity for the β subunit of NKA to a subject in need thereof. Exemplary antibodies that may be used in these methods include, but are not limited to, (i) antibodies having binding specificity for the β$_1$ subunit of NKA, (ii) antibodies having binding specificity for one or more of the peptides represented by SEQ ID NOs:1-4, (iii) antibody JY421228 or a humanized version thereof, or a fragment or derivative thereof, and (iv) antibody JY2948 or a humanized version thereof, or a fragment or derivative thereof. The subject may be one that is characterized has having or at being at greater risk than the general population for one or more of the following diseases and conditions: venous thrombosis, deep vein thrombosis, portal vein thrombosis, renal vein thrombosis, jugular vein thrombosis, Budd-Chiari syndrome, Paget-Schroetter disease, cerebral venous sinus thrombosis, cavernous sinus thrombosis, arterial thrombosis, stroke, pulmonary embolism, coronary heart disease, angina, heart failure, heart valve disease, atherosclerosis, a myocardial infarction, and post-surgical thrombotic complications arising from angioplasty and organ transplantation.

In a fourth aspect, the invention provides methods for inhibiting thrombosis in a subject comprising administering an effective amount of an antibody having binding specificity for the β subunit of NKA to a subject in need thereof. Exemplary antibodies that may be used in these methods include, but are not limited to, (i) antibodies having binding specificity for the β$_1$ subunit of NKA, (ii) antibodies having binding specificity for one or more of the peptides represented by SEQ ID NOs:1-4, (iii) antibody JY421228 or a humanized version thereof, or a fragment or derivative thereof, and (iv) antibody JY2948 or a humanized version thereof, or a fragment or derivative thereof. The subject may be one that is at greater risk than the general population for thrombosis. The subject may be one that is characterized has having or at being at greater risk than the general population for one or more of the following diseases and conditions: venous thrombosis, deep vein thrombosis, portal vein thrombosis, renal vein thrombosis, jugular vein thrombosis, Budd-Chiari syndrome, Paget-Schroetter disease, cerebral venous sinus thrombosis, cavernous sinus thrombosis, arterial thrombosis, stroke, pulmonary embolism, coronary heart disease, angina, heart failure, heart valve disease, atherosclerosis, a myocardial infarction, and post-surgical thrombotic complications arising from angioplasty and organ transplantation.

In a fifth aspect, the invention provides methods for treating thrombosis in a subject comprising administering an effective amount of an antibody having binding specificity for the β subunit of NKA to a subject in need thereof. Exemplary antibodies that may be used in these methods include, but are not limited to, (i) antibodies having binding specificity for the $\beta_1$ subunit of NKA, (ii) antibodies having binding specificity for one or more of the peptides represented by SEQ ID NOs:1-4, (iii) antibody JY421228 or a humanized version thereof, or a fragment or derivative thereof, and (iv) antibody JY2948 or a humanized version thereof, or a fragment or derivative thereof. The subject may be one that is characterized has having or at being at greater risk than the general population for one or more of the following diseases and conditions: venous thrombosis, deep vein thrombosis, portal vein thrombosis, renal vein thrombosis, jugular vein thrombosis, Budd-Chiari syndrome, Paget-Schroetter disease, cerebral venous sinus thrombosis, cavernous sinus thrombosis, arterial thrombosis, stroke, pulmonary embolism, coronary heart disease, angina, heart failure, heart valve disease, atherosclerosis, a myocardial infarction, and post-surgical thrombotic complications arising from angioplasty and organ transplantation.

In a sixth aspect, the invention provides methods for preventing thrombosis in a subject comprising administering an effective amount of an antibody having binding specificity for the β subunit of NKA to a subject in need thereof. Exemplary antibodies that may be used in these methods include, but are not limited to, (i) antibodies having binding specificity for the $\beta_1$ subunit of NKA, (ii) antibodies having binding specificity for one or more of the peptides represented by SEQ ID NOs:1-4, (iii) antibody JY421228 or a humanized version thereof, or a fragment or derivative thereof, and (iv) antibody JY2948 or a humanized version thereof, or a fragment or derivative thereof. The subject may be one that is characterized has having or at being at greater risk than the general population for one or more of the following diseases and conditions: venous thrombosis, deep vein thrombosis, portal vein thrombosis, renal vein thrombosis, jugular vein thrombosis, Budd-Chiari syndrome, Paget-Schroetter disease, cerebral venous sinus thrombosis, cavernous sinus thrombosis, arterial thrombosis, stroke, pulmonary embolism, coronary heart disease, angina, heart failure, heart valve disease, atherosclerosis, a myocardial infarction, and post-surgical thrombotic complications arising from angioplasty and organ transplantation.

In a seventh aspect, the invention provides methods for treating a disease of disregulated platelet aggregation in a subject comprising administering an effective amount of an antibody having binding specificity for the β subunit of NKA to a subject in need thereof. Exemplary antibodies that may be used in these methods include, but are not limited to, (i) antibodies having binding specificity for the $\beta_1$ subunit of NKA, (ii) antibodies having binding specificity for one or more of the peptides represented by SEQ ID NOs:1-4, (iii) antibody JY421228 or a humanized version thereof, or a fragment or derivative thereof, and (iv) antibody JY2948 or a humanized version thereof, or a fragment or derivative thereof. Exemplary diseases of disregulated platelet aggregation include, but are not limited to, hypercoagulability, essential thrombocythemia, reactive thrombocytosis, thrombocytopenia, von Willebrand disease, hereditary intrinsic platelet disorders (e.g., Bernard-Soulier syndrome, May-Hegglin anomaly, Chédiak-Higashi syndrome), and acquired disorders of platelet function (e.g., myeloproliferative and myelodysplastic disorders, uremia, macroglobulinemia, multiple myeloma, cirrhosis).

In each of these aspects, the antibody may be in a pharmaceutical formulation comprising the antibody and a pharmaceutically acceptable carrier.

The foregoing has outlined rather broadly the features and technical advantages of the present invention in order that the detailed description of the invention that follows may be better understood. Additional features and advantages of the invention will be described herein, which form the subject matter of the claims of the invention.

BRIEF DESCRIPTION OF DRAWINGS

FIG. 1A: Isolated platelets+5 µM ADP; FIG. 1B: conditions of 1A+0.2 µM JY2948; FIG. 1C: conditions of 1A+0.2 µM JY421228. All figures have 400× magnification.

FIG. 2A: Human whole blood+5 µM ADP; FIG. 2B: conditions of 2A+0.2 µM JY2948; FIG. 2C: conditions of 2A+0.2 µM JY421228. All figures have 400× magnification.

FIG. 3A—upper curve: Human whole blood+1 µg/ml collagen; FIG. 3A—lower curve: Human whole blood+5 µg/ml collagen. FIG. 3B—upper curve: condition of FIG. 3A—upper curve+0.2 µM JY2948; FIG. 3B—lower curve: condition of FIG. 3A—lower curve+0.2 µM JY2948. FIG. 3C—upper curve: condition of FIG. 3A—upper curve+0.2 µM JY421228. FIG. 3C—lower curve: condition of FIG. 3A—lower curve+0.2 µM JY421228.

FIG. 4A & FIG. 4D: Control background of rat tail before needle stick. FIG. 4B & FIG. 4E: Blood from lateral tail vein after needle stick. FIG. 4C & FIG. 4F: After removal of the blood. FIG. 4G & FIG. 4H: ELISA analyses for generations of endogenous JY2948 (FIG. 4G) or JY421228 (FIG. 4H) antibodies.

DETAILED DESCRIPTION OF THE INVENTION

Figure 1A:
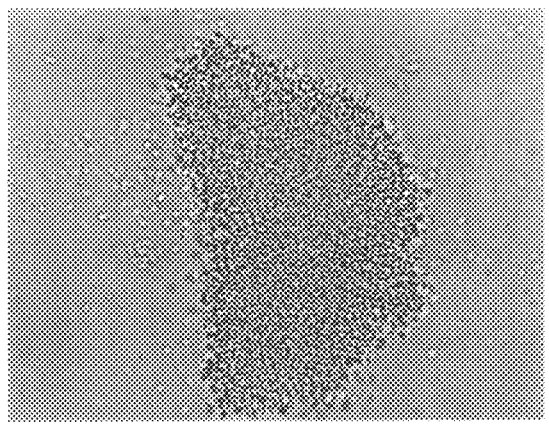
FIGS. 1A-1C. Antibodies JY2948 and JY421228 prevent ADP-induced platelet aggregation in isolated human platelets.

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As outlined in a general manner above, the present invention is based on the surprising discovery that platelet aggregation can be inhibited using antibodies that bind the β subunit of NKA of platelets. Thus, the β subunit binding-antibodies can be used to inhibit platelet activation and aggregation, whether in vitro or in vivo, to inhibit, treat, and prevent thrombosis in a subject, and to treat a disease of disregulated platelet aggregation in a subject. The antibodies also form the basis of methods of treating or preventing blood clots associated with diseases such as stroke, myocardial infarction, deep vein thrombosis, and generally any venous or arterial thrombosis resulting from platelet aggregation and resulting in patient morbidity or mortality.

Antibodies

The skilled artisan will understand that the particular attributes of the antibodies that may be used in the methods of the present invention are only confined by (i) the ability to bind with specificity to the β subunit of NKA, and (ii) the ability to inhibit platelet aggregation.

As described in US2012/0195886 (U.S. Pat. No. 9,040,046), two antibodies have been prepared that specifically bind the $\beta_1$ subunit of NKA, namely antibody JY2948 and antibody JY421228. As shown in the Examples below, these antibodies inhibit platelet aggregation and both of them may be used in the methods of the present invention. Antibody JY2948 binds to amino acids 134-146 of the rat $\beta_1$ subunit of NKA (KERGEFNHERGER; SEQ ID NO:1) and to amino acids 134-146 of the human $\beta_1$ subunit of NKA (KERGDFNHERGER; SEQ ID NO:2). Antibody JY421228 binds to amino acids 218-230 of the rat $\beta_1$ subunit of NKA (RDEDKDKVGNIEY; SEQ ID NO:3) and to amino acids 217-229 of the human $\beta_1$ subunit of NKA (RDEDKDKVGNVEY; SEQ ID NO:4). The invention therefore provides the use of antibody JY2948 and antibody JY421228 in the methods disclosed herein.

The invention also provides the use of antibodies that specifically bind an epitope of the $\beta_1$ subunit of NKA comprising the amino acid sequence KERGEFNHERGER (SEQ ID NO:1; Rat JY2948 epitope), KERGDFNHERGER (SEQ ID NO:2; Human JY2948 epitope), KERGEFNNERGER (SEQ ID NO:5; Dog JY2948 epitope), KERGEYNNERGER (SEQ ID NO:6; Pig JY2948 epitope), or any combination thereof.

The invention further provides for the use of antibodies having binding specificity for an epitope of the $\beta_1$ subunit of NKA comprising the amino acid sequence RDEDKDKVGNIEY (SEQ ID NO:3; Rat JY421228 epitope) or RDEDKDKVGNVEY (SEQ ID NO:4; Human JY421228 epitope), or both.

The invention further provides for the use of antibodies having binding specificity for variants of each of the peptides of SEQ ID NOs:1-6, the variants having 5 or fewer, 4 or fewer, 3 or fewer, 2 or fewer, or 1 amino acid change in comparison to the peptides of SEQ ID NOs:1-6. The changes are each individually selected from insertions, deletions and substitutions. The substitutions may be conservative or non-conservative amino acid substitutions. Each of the variant peptides maintains the ability to induce production of antibodies that specifically bind the β subunit of NKA and that have the ability to inhibit platelet aggregation.

In addition, the invention provides for the use of antibodies having binding specificity for other epitopes of the β subunit of NKA, with those antibodies having binding specificity for other epitopes of the $\beta_1$ subunit of NKA being of particular note.

The antibodies used in the methods of the present invention and defined above may be polyclonal, monoclonal, humanized or chimeric antibodies, and the antibodies may be in the form of an antiserum comprising the antibodies. The antibodies may be of any class, such as IgG1, IgG2, IgG3, IgG4, IgM, IgA1, IgA2, IgD or IgE. The antibodies may be isolated antibodies, purified antibodies, exogenous antibodies, endogenous antibodies, or a combination thereof.

The antibodies may also be antibody fragments of less than the entire antibody, including, but not limited to, single chain antibodies, $F(ab')_2$ fragments, Fab fragments, and fragments produced by an Fab expression library, and derivatives of the antibodies and fragments defined herein, with the only limitation being that the antibody fragments and derivatives retain the ability to bind the β subunit and aggregate platelets. It will thus be clear to the skilled artisan that all references to "antibodies" herein include both full-size antibodies as well as antibody fragments, as defined herein.

The antibodies may be produced in any species of animal, though preferably from a mammal such as a human, simian, mouse, rat, rabbit, guinea pig, horse, cow, sheep, goat, pig, dog or cat. For example, the antibodies can be human antibodies or humanized antibodies, or any antibody preparation suitable for administration to a human. For the production of the antibodies, the selected species of animal can be immunized by injection with one or more of the peptides or variants discussed herein. The peptides and variants may be administered in conjunction with one or more pharmaceutically acceptable adjuvants to increase the immunological response. Suitable adjuvants include, but are not limited to, Freund's Complete and Incomplete Adjuvant, Titermax, Oil in Water Adjuvants, as well as Aluminum compounds where antigens, normally peptides, are physically precipitated with hydrated insoluble salts of aluminum hydroxide or aluminum phosphate. Other adjuvants include liposome-type adjuvants comprising spheres having phospholipid bilayers that form an aqueous compartment containing the peptide and protect it from rapid degradation, and that provide a depot effect for sustained release. Surface active agents may also be used as adjuvants and include lipoteichoic acid of gram-positive organisms, lipid A, and TDM. Quil A and QS-21 (saponin-type adjuvants), monophosphoryl lipid A, and lipophilic MDP derivatives are suitable adjuvants that have hydrophilic and hydrophobic domains from which their surface-active properties arise. Compounds normally found in the body such as vitamin A and E, and lysolecithin may also be used as surface-active agents. Other classes of adjuvants include glycan analog, coenzyme Q, amphotericin B, dimethyldioctadecylammonium bromide (DDA), levamisole, and benzimidazole compounds. The immunostimulation provided by a surface active agent may also be accomplished by either developing a fusion protein with non-active portions of the cholera toxin, exotoxin A, or the heat labile toxin from *E. coli*. Immunomodulation through the use of anti-IL-17, anti IFN-γ, anti-IL-12, IL-2, IL-10, or IL-4 may also be used to promote a strong Th2 or antibody mediated response to the immunogenic formulation.

Means for preparing antibodies are very well known in the art. The antibodies of the invention can be prepared using any known technique that provides for the production of antibody molecules. Suitable techniques include, but are not limited to, the hybridoma technique originally described by Koehler and Milstein (Nature 256:495-497 (1975)), the human B-cell hybridoma technique (Kosbor et al., Immunol Today 4:72 (1983); Cote et al., Proc Natl. Acad. Sci 80:2026-2030 (1983)), and the EBV-hybridoma technique (Cole et al., Monoclonal Antibodies and Cancer Therapy, Alan R. Liss Inc, New York N.Y., pp 77-96 (1985)). Each of these publications is herein incorporated by reference in its entirety. Additionally, antibodies can be produced by inducing in vivo production in the lymphocyte population or by screening recombinant immunoglobulin libraries or panels of highly specific binding reagents as disclosed in Orlandi et al., *Proc Natl. Acad. Sci. USA* 86: 3833-3837 (1989), and in Winter G. and Milstein C., *Nature* 349:293-299 (1991), both of which is herein incorporated by reference in its entirety.

Humanized antibodies are those where a human antibody has been engineered to contain non-human complementarity-determining regions (CDRs) derived from an antibody produced in a non-human host against a selected antigen. Means for producing humanized antibodies are well-known in the art and include Vaswani S K, and Hamilton R G, *Ann Allergy Asthma Immunol.* 81(2):105-15 (1998) and Kashmiri S V et al., *Methods* 36 (1):25-34 (2005), each of which is herein incorporated by reference in its entirety.

Chimeric antibodies are those where an antigen binding region (e.g., F(ab')$_2$ or hypervariable region) of a non-human antibody is transferred into the framework of a human antibody by recombinant DNA techniques. Techniques developed for the production of such antibodies include the splicing of mouse antibody genes to human antibody genes to obtain a molecule with appropriate antigen specificity and biological activity. Such techniques are also well known and include: Morrison et al., *Proc Natl. Acad. Sci* 81:6851-6855 (1984); Neuberger et al., *Nature* 312:604-608(1984); Takeda et al., *Nature* 314:452-454(1985), each of which is herein incorporated by reference in its entirety.

Techniques for the production of single chain antibodies are described in U.S. Pat. No. 4,946,778, incorporated herein by reference in its entirety.

Antibody fragments such as F(ab')$_2$ fragments can be produced by pepsin digestion of the antibody molecule, and Fab fragments can be generated by reducing the disulfide bridges of the F(ab')$_2$ fragments. Alternatively, Fab expression libraries can be constructed to allow rapid and easy identification of monoclonal Fab fragments with the desired specificity (Huse W. D. et al., Science 256:1275-1281 (1989), herein incorporated by reference in its entirety).

The invention provides for the use of pharmaceutical formulations comprising one or more of the antibodies of the invention and a pharmaceutically acceptable carrier. Such formulations may be administered to a subject when practicing the methods of the present invention. Suitable examples of carriers are well known to those skilled in the art and include water, water-for-injection, saline, buffered saline, dextrose, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, hydrophilic and hydrophobic carriers, and combinations thereof. Hydrophobic carriers include, for example, fat emulsions, lipids, PEGylated phospholipids, polymer matrices, biocompatible polymers, lipospheres, vesicles, particles, and liposomes. The terms specifically exclude cell culture medium. The formulations may further comprise stabilizing agents, buffers, antioxidants and preservatives, tonicity agents, bulking agents, emulsifiers, suspending or viscosity agents, inert diluents, fillers, and combinations thereof.

The identity of the carrier(s) will also depend on the means used to administer pharmaceutical formulations comprising antibodies to a subject. For example, pharmaceutical formulations for intramuscular preparations can be prepared where the carrier is water-for-injection, 0.9% saline, or 5% glucose solution. Pharmaceutical formulations may also be prepared as liquid or powdered atomized dispersions for delivery by inhalation. Such dispersion typically contain carriers common for atomized or aerosolized dispersions, such as buffered saline and/or other compounds well known to those of skill in the art. The delivery of the pharmaceutical formulations via inhalation has the effect of rapidly dispersing the vaccine formulation to a large area of mucosal tissues as well as quick absorption by the blood for circulation. One example of a method of preparing an atomized dispersion is described in U.S. Pat. No. 6,187,344, entitled, "Powdered Pharmaceutical Formulations Having Improved Dispersibility," which is hereby incorporated by reference in its entirety.

Additionally, the pharmaceutical formulations may also be administered in a liquid form. The liquid can be for oral dosage, for ophthalmic or nasal dosage as drops, or for use as an enema or douche. When the pharmaceutical formulation is formulated as a liquid, the liquid can be either a solution or a suspension of the pharmaceutical formulation. There is a variety of suitable formulations for the solution or suspension of the pharmaceutical formulations that are well known to those of skill in the art, depending on the intended use thereof. Liquid formulations for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents.

Methods for Inhibiting Platelet Aggregation

As indicated above, the present invention includes methods for inhibiting platelet aggregation. This method comprising contacting platelets with an antibody having binding specificity for the β subunit of NKA. It will be apparent to the skilled artisan that this method can be practice in vitro, in vivo and ex vivo (e.g., in blood flowing through a heart bypass machine during surgery).

Any of the antibodies described herein, whether polyclonal or monoclonal, can be used in the method, as well as humanized or chimeric versions of the antibodies, and fragments of any of these. Exemplary antibodies that may be used in these methods include, but are not limited to, (i) antibodies having binding specificity for the $\beta_1$ subunit of NKA, (ii) antibodies having binding specificity for one or more of the peptides represented by SEQ ID NOs:1-4, (iii) antibody JY421228 or a humanized version thereof, and (iv) antibody JY2948 or a humanized version thereof.

Methods for Inhibiting Platelet Activation

The present invention includes methods for inhibiting platelet activation. This method comprising contacting platelets with an antibody having binding specificity for the β subunit of NKA. It will be apparent to the skilled artisan that this method can be practice in vitro, in vivo and ex vivo (e.g., in blood flowing through a heart bypass machine during surgery). Any of the antibodies described herein, whether polyclonal or monoclonal, can be used in the method, as well as humanized or chimeric versions of the antibodies, and fragments of any of these. Exemplary antibodies that may be used in these methods include, but are not limited to, (i) antibodies having binding specificity for the $β_1$ subunit of NKA, (ii) antibodies having binding specificity for one or more of the peptides represented by SEQ ID NOs:1-4, (iii) antibody JY421228 or a humanized version thereof, and (iv) antibody JY2948 or a humanized version thereof.

Methods of Treatment

The invention also provides methods for treating or preventing particular diseases, disorders and conditions in a subject by inhibiting platelet aggregation.

The invention thus includes methods for inhibiting platelet aggregation in a subject comprising administering an effective amount of an antibody having binding specificity for the β subunit of NKA to a subject in need thereof. While the subject is not limited to one having a particular disease or condition, the subject may be one that is characterized has having or at being at greater risk than the general population for one or more of the following diseases and conditions: venous thrombosis, deep vein thrombosis, portal vein thrombosis, renal vein thrombosis, jugular vein thrombosis, Budd-Chiari syndrome, Paget-Schroetter disease, cerebral venous sinus thrombosis, cavernous sinus thrombosis, arterial thrombosis, stroke, pulmonary embolism, coronary heart disease, angina, heart failure, heart valve disease, atherosclerosis, myocardial infarction, and post-surgical thrombotic complications arising from angioplasty and organ transplantation or other disease or condition wherein inhibition of platelet aggregation would be desirable or necessary.

The invention includes methods for inhibiting, treating or preventing thrombosis in a subject, where the method comprises administering an effective amount of an antibody having binding specificity for the β subunit of NKA to a subject in need thereof. While the subject is not limited to one having a particular disease or condition, the subject may be one that is characterized has having or at being at greater risk than the general population for one or more of the following diseases and conditions: venous thrombosis, deep vein thrombosis, portal vein thrombosis, renal vein thrombosis, jugular vein thrombosis, Budd-Chiari syndrome, Paget-Schroetter disease, cerebral venous sinus thrombosis, cavernous sinus thrombosis, arterial thrombosis, stroke, pulmonary embolism, coronary heart disease, angina, heart failure, heart valve disease, atherosclerosis, myocardial infarction, and post-surgical thrombotic complications arising from angioplasty and organ transplantation or other disease or condition wherein inhibition of platelet aggregation would be desirable or necessary.

The invention also includes methods for treating a disease of disregulated platelet aggregation in a subject comprising administering an effective amount of an antibody having binding specificity for the β subunit of NKA to a subject in need thereof. Exemplary diseases of dysregulated platelet aggregation include, but are not limited to, hypercoagulability, essential thrombocythemia, reactive thrombocytosis, thrombocytopenia, von Willebrand disease, hereditary intrinsic platelet disorders (e.g., Bernard-Soulier syndrome, May-Hegglin anomaly, Chédiak-Higashi syndrome), and acquired disorders of platelet function (e.g., myeloproliferative and myelodysplastic disorders, uremia, macroglobulinemia, multiple myeloma, cirrhosis).

Any of the antibodies described herein, whether polyclonal or monoclonal, can be used in the method, as well as humanized or chimeric versions of the antibodies, and fragments and derivatives of any of these. Exemplary antibodies that may be used in these methods include, but are not limited to, (i) antibodies having binding specificity for the $β_1$ subunit of NKA, including isoform of $β_1$ subunit, (ii) antibodies having binding specificity for one or more of the peptides represented by SEQ ID NOs:1-6, (iii) antibody JY421228 or a humanized version thereof, or a fragment or derivative thereof, and (iv) antibody JY2948 or a humanized version thereof, or a fragment or derivative thereof. The antibody may be administered as a pharmaceutical formulation comprising the antibody and a pharmaceutically acceptable carrier.

As used herein, the terms "treat", "treating" and "treatment" have their ordinary and customary meanings, and include one or more of, ameliorating thrombosis or a disease of dysregulated platelet aggregation, ameliorating a symptom of thrombosis or a disease of dysregulated platelet aggregation, or decreasing in severity and/or frequency a symptom of thrombosis or a disease of dysregulated platelet aggregation. Treatment means ameliorating or decreasing by about 1% to about 100% versus a subject to which the antibody has not been administered. Preferably, the ameliorating or decreasing or inhibiting is about 100%, about 99%, about 98%, about 97%, about 96%, about 95%, about 90%, about 80%, about 70%, about 60%, about 50%, about 40%, about 30%, about 20%, about 10%, about 5% or about 1%. The treatment may begin prior to, concurrent with, or after the onset of clinical symptoms of thrombosis or a disease of dysregulated platelet aggregation. The results of the treatment may be permanent or may continue for a period of days (such as 1, 2, 3, 4, 5, 6 or 7 days), weeks (such as 1, 2, 3 or 4 weeks) or months (such as 1, 2, 3, 4, 5, 6 or more months).

As used herein, the terms "prevent", "preventing" and "prevention" have their ordinary and customary meanings, and include one or more of, stopping, averting, avoiding or blocking thrombosis, the occurrence of a symptom of thrombosis, the recurrence of a symptom of thrombosis, the development of thrombosis or the progression of thrombosis. Prevention means stopping by at least about 95% versus a subject to which the antibody has not been administered. Preferably, the stopping is about 100%, about 99%, about 98%, about 97%, about 96% or about 95%. The results of the prevention may be permanent or may continue for a period of days (such as 1, 2, 3, 4, 5, 6 or 7 days), weeks (such as 1, 2, 3 or 4 weeks) or months (such as 1, 2, 3, 4, 5, 6 or more months).

As used herein, the terms "inhibit", "inhibiting" and "inhibition" have their ordinary and customary meanings, and include one or more of, hindering, impeding, obstructing, deterring or restraining platelet aggregation or thrombosis, the occurrence of a symptom of platelet aggregation or thrombosis, the recurrence of a symptom of platelet aggregation or thrombosis, the development of platelet aggregation or thrombosis, or the progression of platelet aggregation or thrombosis. Inhibition means impeding by about 1% to about 100% versus a subject to which the antibody has not been administered. Preferably, the impeding is about 100%, about 99%, about 98%, about 97%, about 96%, about 95%, about 90%, about 80%, about 70%, about 60%, about 50%, about 40%, about 30%, about 20%, about 10%, about 5% or about 1%. The course of therapy may begin prior to, concurrent with, or after the onset of clinical symptoms of platelet aggregation or thrombosis. Thus, the subject may have platelet aggregation or thrombosis, or merely be susceptible to platelet aggregation or thrombosis. The results of the inhibition may be permanent or may continue for a period of days (such as 1, 2, 3, 4, 5, 6 or 7 days), weeks (such as 1, 2, 3 or 4 weeks) or months (such as 1, 2, 3, 4, 5, 6 or more months).

The antibodies and formulations may be administered to a subject using different schedules, depending on the particular aim or goal of the method; the age and size of the subject; and the general health of the subject, to name only a few factors to be considered. In general, the antibodies and formulations may be administered once, or twice, three times, four times, five times, six times or more, over a course of treatment, inhibition or prevention. The timing between each dose in a dosing schedule may range between days, weeks, months, or years, an includes administered once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more weeks. The same quantity of antibody may be administered in each dose of the dosing schedule, or the amounts in each dose may vary. The identity of the particular antibody may also vary or remain the same in each dose in a dosing schedule.

In each of the methods of the present invention, an "effective amount" of an antibody or a pharmaceutical formulation comprising an antibody is administered to a subject. The effective amount will vary between subjects. However, the effective amount is one that is sufficient to achieve the aim or goal of the method, whether inhibiting, treating or preventing. As an example, an effective amount of an antibody used in the methods of the invention is typically between about 0.1 µg to about 1000 µg of antibody per kg of body weight of the subject to which the antibody is administered. An effective amount also includes between about 1 µg to about 500 µg, between about 10 µg to about 200 µg, between about 1 µg to about 800 µg, between about 10 µg to about 800 µg, between about 1 µg to about 300 µg, and between about 10 µg to about 300 µg of antibody per kg of body weight of the subject.

Appropriate doses and dosing schedules can readily be determined by techniques well known to those of ordinary skill in the art without undue experimentation. Such a determination will be based, in part, on the tolerability and efficacy of a particular dose.

Administration of the antibody or formulation may be via any of the means commonly known in the art of antibody delivery. Such routes include intravenous, intraperitoneal, intramuscular, subcutaneous and intradermal routes of administration, as well as nasal application, by inhalation, ophthalmically, orally, rectally, vaginally, or by any other mode that results in the antibody or formulation contacting mucosal tissues.

The term "subject" is intended to mean an animal, such birds or mammals, including humans and animals of veterinary or agricultural importance, such as dogs, cats, horses, sheep, goats, and cattle.

A kit comprising the necessary components for practicing the methods of the invention, including an antibody or a pharmaceutical formulation comprising an antibody, and instructions for its use is also within the purview of the present invention.

It is understood that the examples and embodiments described herein are for illustrative purposes only and that various modifications or changes in light thereof will be suggested to persons skilled in the art and are to be included within the spirit and purview of this application and scope of the appended claims.

All documents, papers and published materials referenced herein, including books, journal articles, manuals, patent applications, published patent applications and patents, are expressly incorporated herein by reference in their entireties.

EXAMPLES

Inhibition of ADP-Induced Platelet Activation and Aggregation

Materials: ZEISS Axioskop microscope, Micro cover glass, Microscope slides, 1 mM ADP, human blood, and isolated human platelets. Method-1: Preparation of platelet-rich plasma (PRP): Human blood was collected from a healthy volunteer who was not on any medications. PRP was prepared by centrifuging blood at 100 g for 20 min at room temperature (with no brake applied) using a Sonvall Legend X1R centrifuge (Thermo Scienfific). After the spin, three distinct layers were observed. The top straw-colored layer was used as PRP. Method-2: Detection of ADP induced platelet aggregation: Fresh-made PRP (FIG. 1A-1C) or whole blood (FIG. 2A-2C) were incubated with or without antibody JY2948 or JY421228 for 60 minutes at room temperature followed by addition of 0.2 µM ADP. Experimental sample (10 µl each) was taken from the reaction mixture on to a microscope slide and covered by a micro cover glass. Platelet aggregation and the prevention of its aggregation were detected by a ZEISS Axioskop microscope.

Figure 1B:
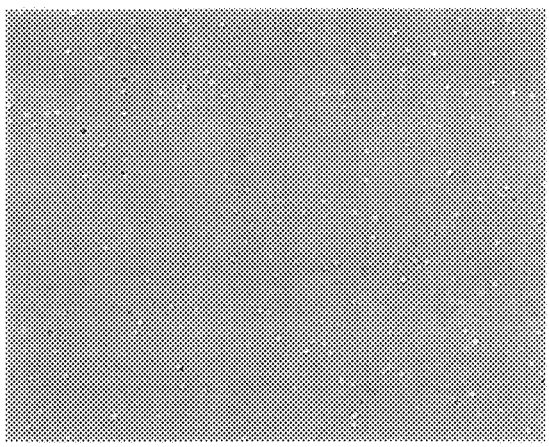
Figure 1C:
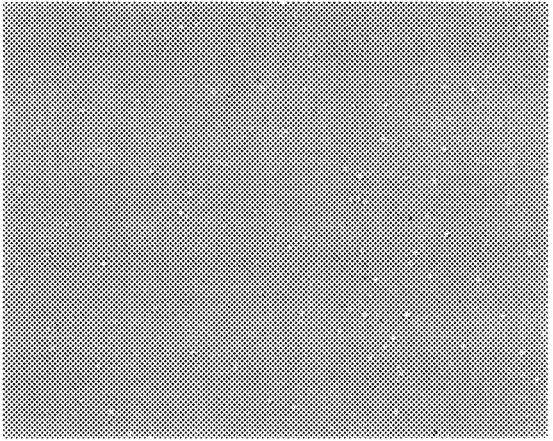
Figure 2A:
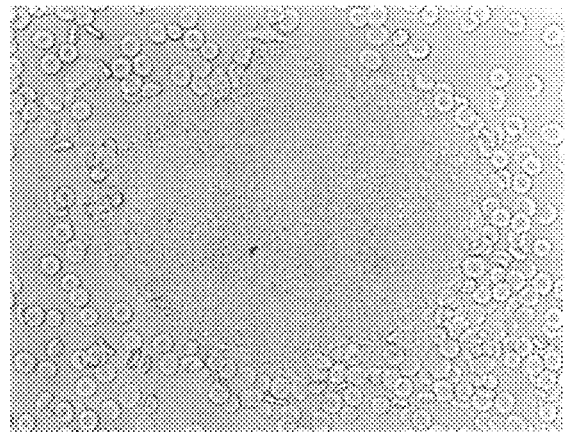
FIGS. 2A-2C. Antibodies JY2948 and JY421228 prevent ADP-induced platelet aggregation in whole blood.
Figure 2B:
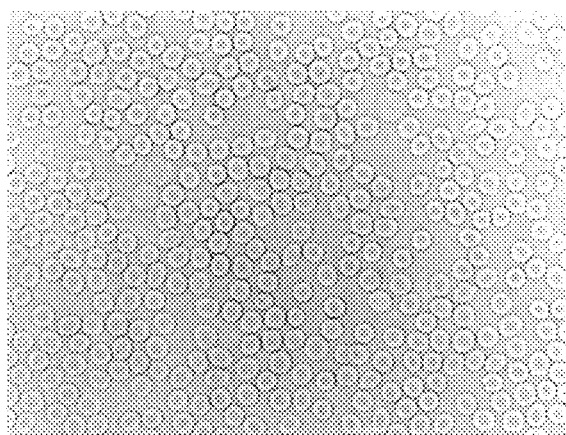
Figure 2C:
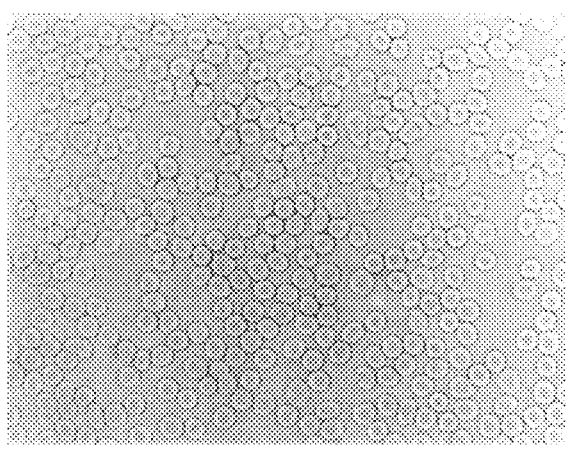

As shown in FIG. 1A, 5 µM ADP induced activation and aggregation in an isolated culture of human platelets. In distinct contrast, 0.2 µM mAb JY2948 (FIG. 1B) or mAb JY421228 (FIG. 1C) prevented platelet activation and aggregation in the presence of ADP. Similar results were found when testing on human whole blood level, ADP induced platelet activation and aggregation as shown in FIG. 2A and both JY2948 (FIG. 2B) and JY421228 (FIG. 2C) prevented the formation of platelet aggregation.

Platelet Inhibition in the Presence of Collagen

Materials: Aggregometer (Chrono-Log Corporation), isotonic saline, collagen (1 mg/ml), and human blood. Method: Impedance measurement: Electrical impedance aggregation measurements were performed on an aggregometer (Chrono-Log Corporation, 560 model), which was equipped with automated calibration and readout functions. The instrument was maintained according to the manufacturer instructions for proper cleaning and maintenance of the electrode. The blood sample (0.5 mL each) was incubated with or without antibody JY2948 or JY421228 (0.2 µM) for 60 minutes at room temperature prior to be diluted with an equivalent volume of isotonic saline and incubated for 5 minutes at 37° C. The impedance of each sample was monitored in sequential 1-minute intervals until a stable baseline was established. After a stable baseline was established, the collagen was added to the sample, aggregation was monitored for approximately 8-11 minutes, and the final increase in ohms over this period was displayed as a numeric LED readout. In addition, a graphical printout (i.e., chart tracing) of each electrical impedance aggregometry tracing was obtained.

Figure 3A:
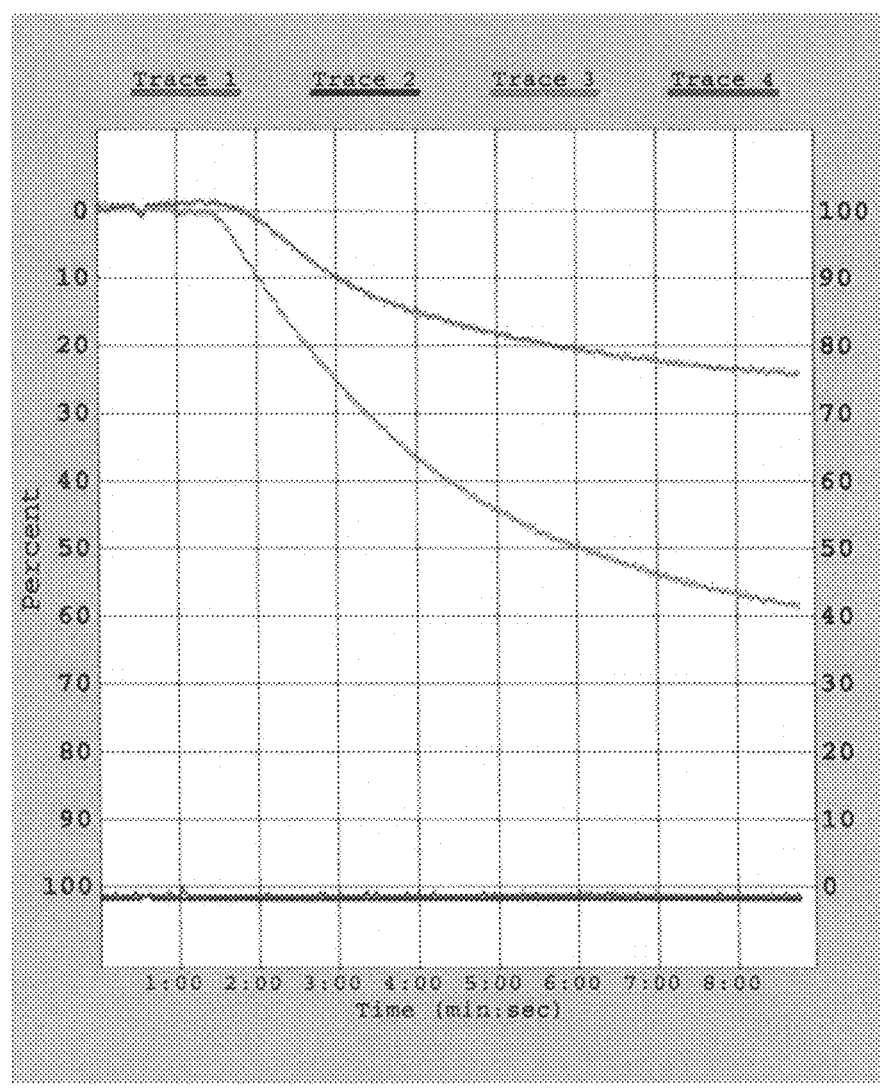
FIGS. 3A-3C. Antibodies JY2948 and JY421228 prevent platelet aggregation in the presence of collagen.
Figure 3B:
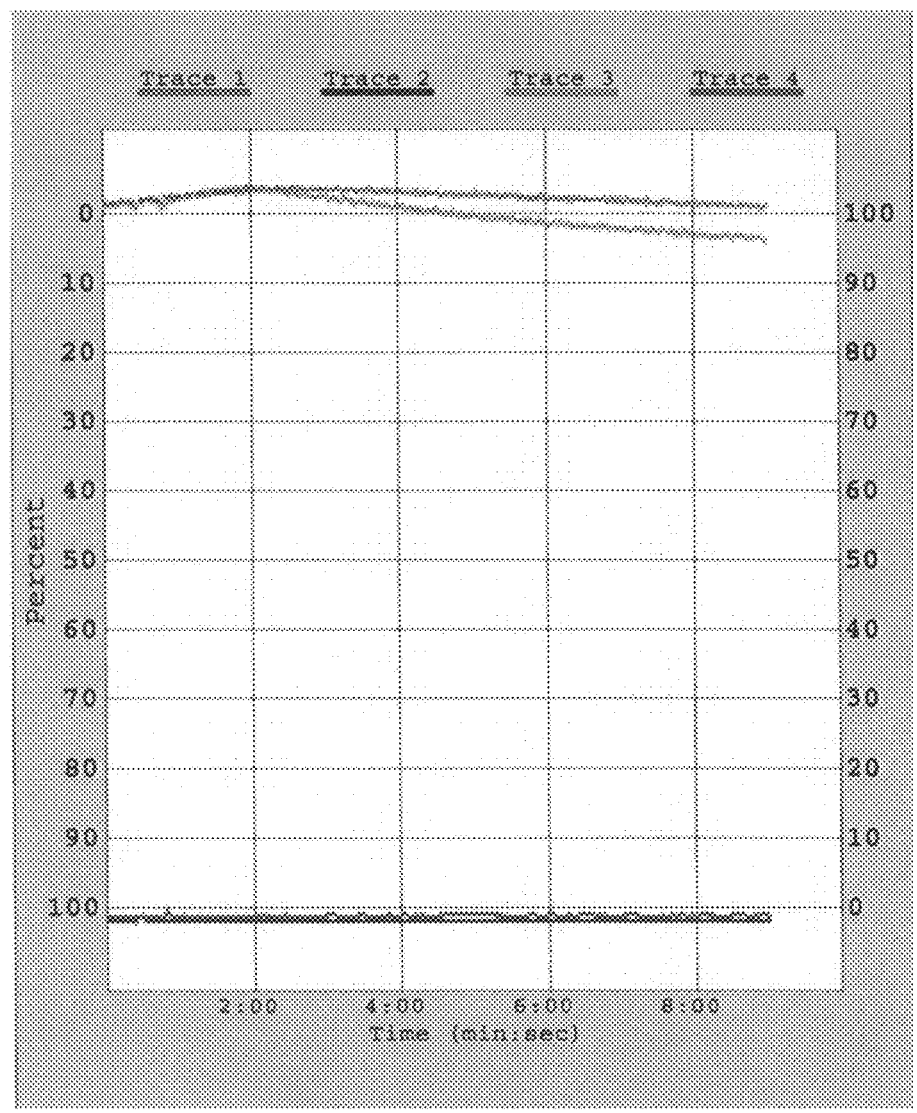
Figure 3C:
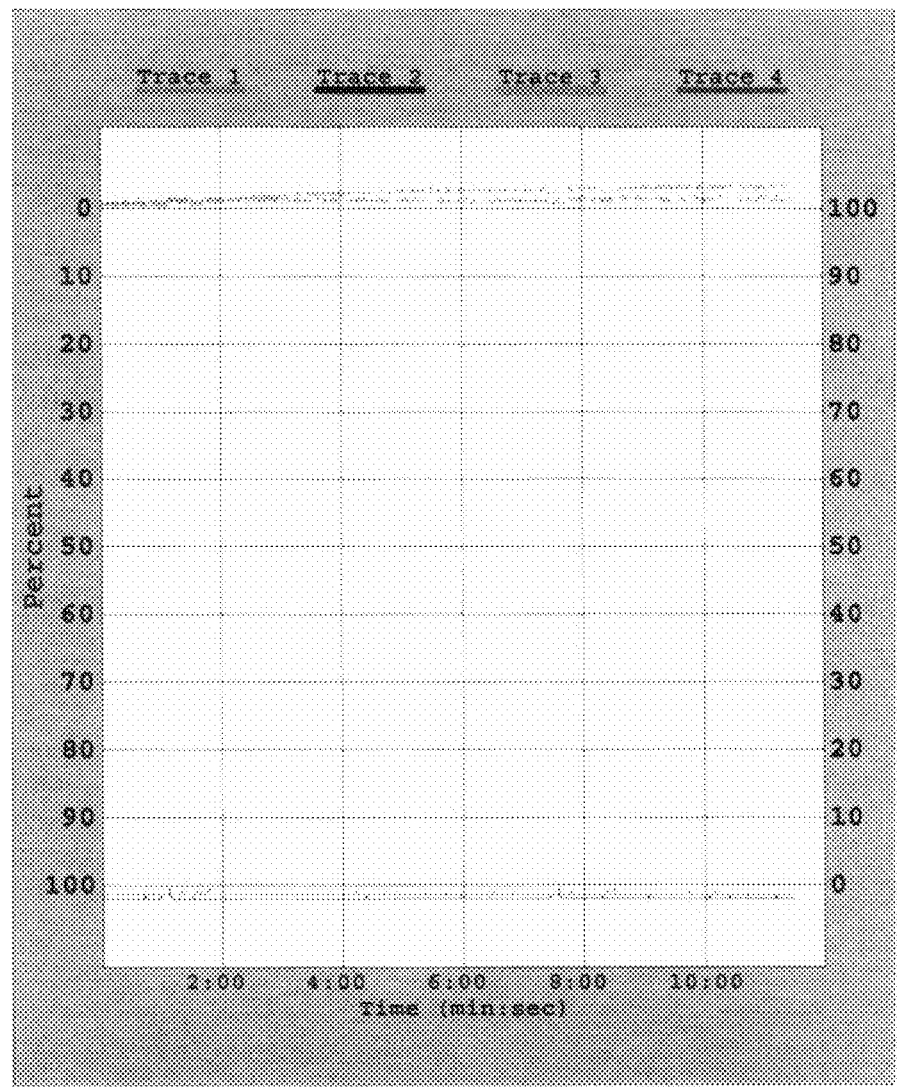

As shown in FIG. 3A, both 1 (upper curve) and 5 (lower curve) μg/ml collagen induced platelet aggregation. However, JY2948 (FIG. 3B) and JY421228 (FIG. 3C) (0.2 μM each) significantly inhibited platelet activation and aggregation, demonstrating that both JY2948 and JY421228 antibodies have the capability to prevent platelet aggregation, which may be potentially used to prevent and treat thrombosis and its associated disorders, including stroke, myocardial infarction and pulmonary embolism.

Bleeding Tests

Figures 4A, 4B, 4C, 4D, 4E, 4F:
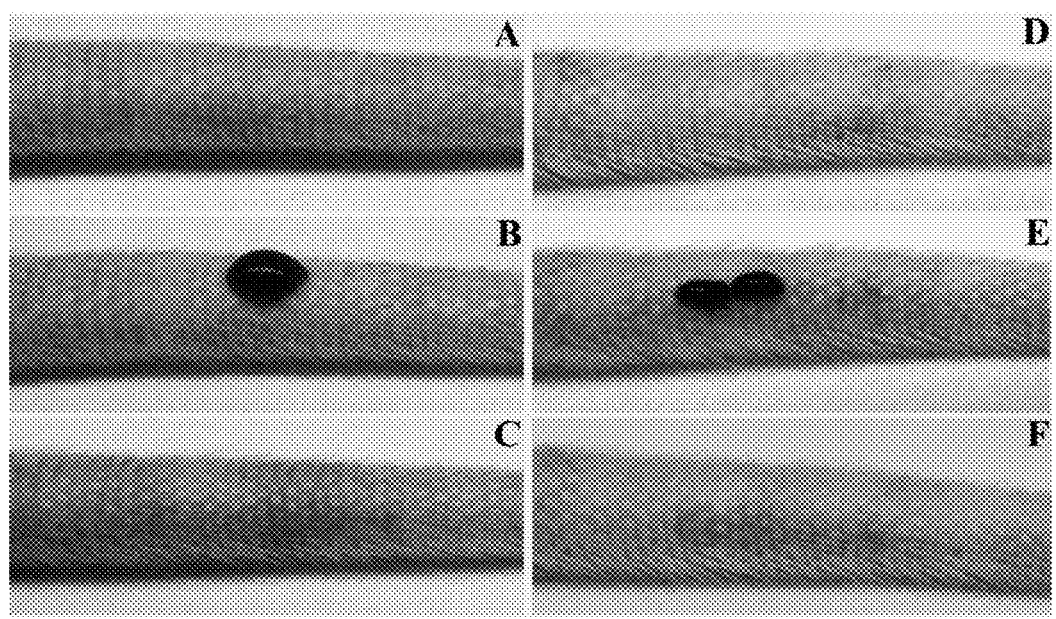
FIGS. 4A-4H. Antibodies JY2948 and JY421228 do not cause bleeding (n=5/each group). Representative Rat 1 (FIG. 4A, FIG. 4B & FIG. 4C) and Rat 2 (FIG. 4D, FIG. 4E & FIG. 4F) were immunized with antigen of JY2948 and JY421228, respectively. A quick bleeding test was performed at rat lateral tail vein.
Figures 4G, 4H:
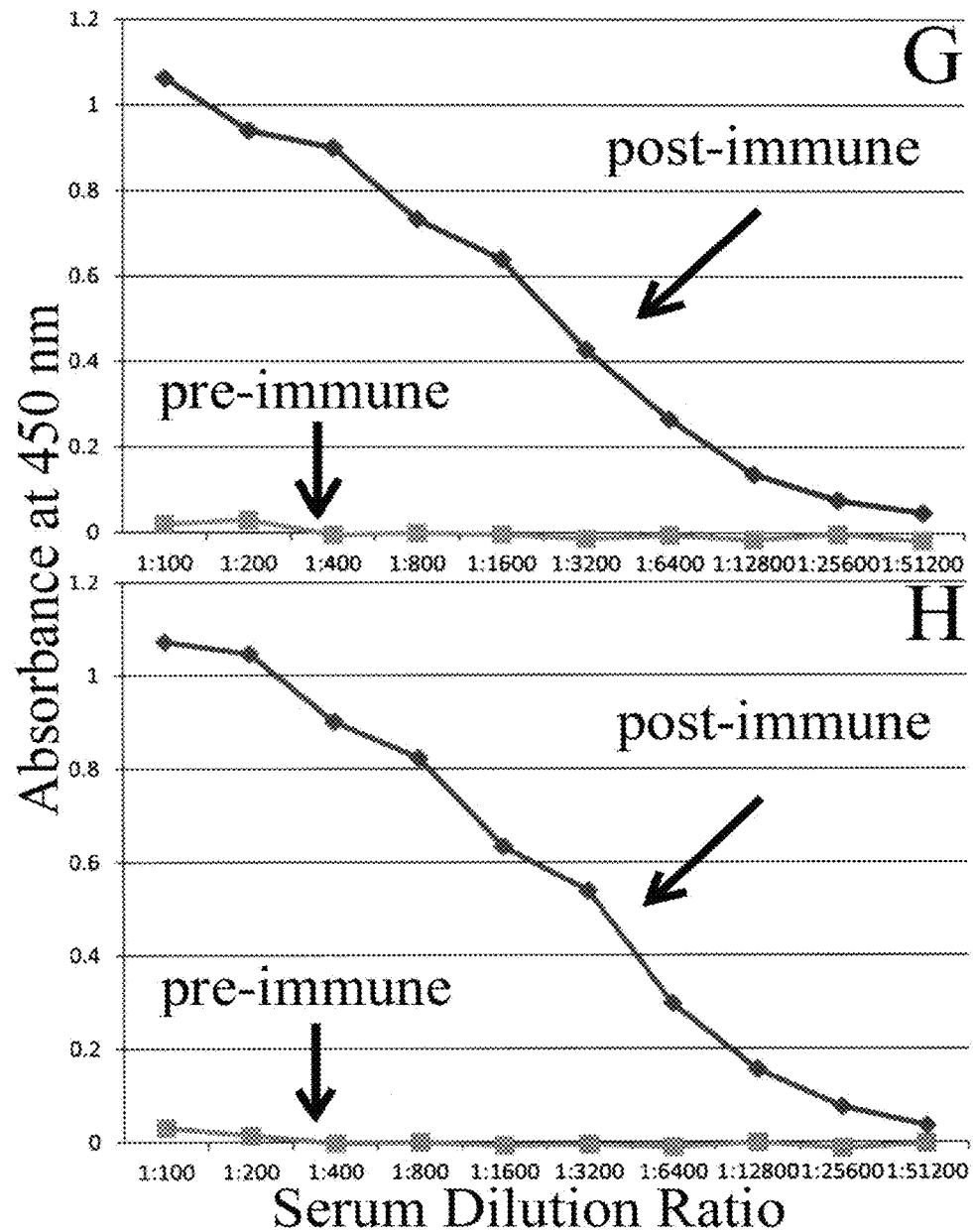

Rats were immunized with antigen JY2948 (KERGEFN-HERGER; SEQ ID NO:1) or JY421228 (RDEDKDK-VGNIEY; SEQ ID NO:3) separately for two months. ELISA assay analyses demonstrated the generation of JY2948 antibody with an antibody titer over 1:4800 (FIG. 4G) and JY421228 antibody with an antibody titer over 1:6400 (FIG. 4H).

A bleeding test was performed at the rat lateral tail vein. Representative Rat 1 (FIGS. 4A-4C) and Rat 2 (FIGS. 4D-4F) immunized with antigen JY2948 and JY421228, respectively. FIGS. 4A & 4D: Control background of rat tail before needle stick. FIGS. 4B & 4E: Blood from lateral tail vein after needle stick. FIGS. 4C & 4F: After removal of the blood. Time length of the bleeding test from beginning and finish was 5-6 seconds. Five Rats were used per each group and all rats had similar results. Antibodies JY2948 and JY421228 were thus found to not increase bleeding in experimental animals.

Antibody Involvement in Conventional Drug Pathways

| Drug Name | Irreversible Binding | Inhibition of Clotting Factors | Inhibition of Forming Thrombin | Inhibition of IIB/IIIa Pathways |
|---|---|---|---|---|
| Aspirin | Yes | | | |
| Clopidogrel | Yes | | | |
| Abciximab | Yes | | | |
| Coumarins | | Yes | | |
| Hirudin | | | Yes | |
| Argatroban | | | Yes | |
| Tirofiban | | | | Yes |
| Eptifibatide | | | | Yes |
| JY2948, JY421228 | No | No | No | No |

What is claimed is:

1. A method of inhibiting thrombosis in a subject comprising administering an effective amount of an antibody that specifically binds an epitope of the $\beta_1$ subunit of the $(Na^+ + K^+)$-ATPase to a subject in need thereof, said epitope is represented by SEQ ID NOS: 1-4.

2. The method of claim 1, wherein the antibody is a polyclonal antibody, monoclonal antibody, or humanized antibody thereof.

3. The method of claim 1, wherein the subject has or is at greater risk than the general population for a disease or condition selected from the group consisting of venous thrombosis, deep vein thrombosis, portal vein thrombosis, renal vein thrombosis, jugular vein thrombosis, Budd-Chiari syndrome, Paget-Schroetter disease, cerebral venous sinus thrombosis, cavernous sinus thrombosis, arterial thrombosis, stroke, pulmonary embolism, coronary heart disease, angina, heart failure, heart valve disease, atherosclerosis, a myocardial infarction, and post-surgical thrombotic complications arising from angioplasty and organ transplantation.

* * * * *

SEQUENCE LISTING

```
<160> NUMBER OF SEQ ID NOS: 6

<210> SEQ ID NO 1
<211> LENGTH: 13
<212> TYPE: PRT
<213> ORGANISM: Rattus rattus

<400> SEQUENCE: 1

Lys Glu Arg Gly Glu Phe Asn His Glu Arg Gly Glu Arg
1               5                   10

<210> SEQ ID NO 2
<211> LENGTH: 13
<212> TYPE: PRT
<213> ORGANISM: Homo sapiens

<400> SEQUENCE: 2

Lys Glu Arg Gly Asp Phe Asn His Glu Arg Gly Glu Arg
1               5                   10

<210> SEQ ID NO 3
<211> LENGTH: 13
<212> TYPE: PRT
<213> ORGANISM: Rattus rattus

<400> SEQUENCE: 3

Arg Asp Glu Asp Lys Asp Lys Val Gly Asn Ile Glu Tyr
1               5                   10

<210> SEQ ID NO 4
<211> LENGTH: 13
<212> TYPE: PRT
<213> ORGANISM: Homo sapiens

<400> SEQUENCE: 4

Arg Asp Glu Asp Lys Asp Lys Val Gly Asn Val Glu Tyr
1               5                   10

<210> SEQ ID NO 5
```

```
<211> LENGTH: 13
<212> TYPE: PRT
<213> ORGANISM: Canis familiaris

<400> SEQUENCE: 5

Lys Glu Arg Gly Glu Phe Asn Asn Glu Arg Gly Glu Arg
1               5                   10

<210> SEQ ID NO 6
<211> LENGTH: 13
<212> TYPE: PRT
<213> ORGANISM: Sus scrofa

<400> SEQUENCE: 6

Lys Glu Arg Gly Glu Tyr Asn Asn Glu Arg Gly Glu Arg
1               5                   10
```